United States Patent
Chung

(10) Patent No.: US 7,273,705 B2
(45) Date of Patent: Sep. 25, 2007

(54) APPARATUS AND METHOD FOR SEPARATING RIBONUCLEIC ACID

(75) Inventor: Yung-Chiang Chung, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 161 days.

(21) Appl. No.: 10/704,707

(22) Filed: Nov. 12, 2003

(65) Prior Publication Data

US 2005/0059027 A1    Mar. 17, 2005

(51) Int. Cl.
*C12P 1/68* (2006.01)
*C07H 21/04* (2006.01)

(52) U.S. Cl. .................. 435/6; 536/24.31; 536/24.32

(58) Field of Classification Search .............. 435/6, 435/287.2; 536/22.1, 23.1, 24.32, 24.31
See application file for complete search history.

(56) References Cited

U.S. PATENT DOCUMENTS 5,413,708 A * 5/1995 Huse et al. .............. 210/198.2
5,482,834 A * 1/1996 Gillespie ..................... 435/6

OTHER PUBLICATIONS

Krishnan et al. Microfabricated reaction and separation systems. Current Opinion in Biotechnology, vol. 12, p. 92-98, 2001.*
Cheng et al. Preparation and hybridization analysis of DNA/RNA from *E.coli* on microfabricated bioelectronic chips. Nature Biotechnology, vol. 16, pp. 541-546, 1998.*

* cited by examiner

*Primary Examiner*—Suryaprabha Chunduru
(74) *Attorney, Agent, or Firm*—Birch, Stewart, Kolasch & Birch, LLP

(57) ABSTRACT

An RNA separation method includes injecting a reaction solution into a reaction region which contains a covalent linking of specific RNA probe for hybridizing with the reaction solution; adjusting a moderate hybridization temperature in the reaction region; moving the remainder of the reaction solution to a transition region by using a pneumatic actuator; adding a buffer solution to the reaction region, and heating the reaction region to a moderate denature temperature by a heating apparatus; moving a waste solution which is product produced from the reaction region after denature to a waste region by using the pneumatic actuator; and moving the remainder solution back to the reaction region by the pneumatic actuator.

8 Claims, 9 Drawing Sheets

APPARATUS AND METHOD FOR SEPARATING RIBONUCLEIC ACID

BACKGROUND OF THE INVENTION (a). Field of the Invention

The present invention relates to a device and a method for RNA separation, more particularly, to a device and a method capable of rapidly purifying mRNA for prokaryotic cells.

(b). Description of the Prior Arts

Up to today, biotechnology development is already having a significant advance on biochemical analysis. It is clear that the knowledge of those molecular biology techniques provide a powerful resource for studying biological processes, and it is also cleaning the way for future research. In particular, we can know more detail about different pathogens, such as facts about bacteria and virus, development and process of disease variation, even the amplification and exhibition of human cells, basing on gene modulation and exhibition.

In order to efficiently study the gene expression, a way must be developed to purify the mRNA of target gene of cell or pathogenesis. After then, we can advance to know the physiological and biochemical roles of target genes according to the quantity, the length of half life and the mechanism of biochemical interaction. There are three kinds of ribonucleic acid, such as the message ribonucleic acid, ribosome ribonucleic acid and transfer ribonucleic acid in the prokaryotic and eukaryotic cells. But the amount of mRNA is much less than the tRNA and rRNA. Therefore, a special biotechnology is needed to isolate the mRNA.

Most of the previous methods for isolating mRNA can be divided into two steps, i.e. the total RNA extraction and the mRNA purification. The mechanism of total RNA extraction is based on that deoxyribonucleic acid will denature at lower pH 7 and protein will also denature in the phenol, therefore, the DNA and protein will denature and combine together in the acid phenol solution. The traditional protocol of preparation of total RNA is to pellet up to $10^7$ cells in a suitable tube by centrifugation at 400 g for 5 min at 4° C. After the supernatant is being poured off, the pellet is disrupted by flicking the base of the tube and therefore the cells are re-suspended in the Trizol reagent. Afterward, the cells are transferred to a microcentrifuge tube and incubated in the Trizol for 5 min at room temperature, further, the cells are stirred occasionally to ensure that cells are completely disrupted. Following, to each 0.5 ml of cells in Trizol, adding 10 ul of chloroform, mixing well by shaking the solution for 15 second and leaving at room temperature for 2-3 min, then the solution is centrifuge at 14,500 g for 15 min at 4° C. In order to take the upper aqueous phase that contains the RNA to a new tube, first, 250 ul isopropanol is added to the centrifuged solution and keeps thereof at 4° C. following by pouring off the supernatant, re-spinning for 1 min and removing the residual supernatant. Secondly, the pellet is washed with 1 ml 75% ethanol, and is stirred and centrifuged at 9,000 g for 5 min at 4° C. Finally, removing the ethanol, allowing the pellet to air dry, and re-suspending the pellet in 75 ul of double-deionized, RNase-free water.

The total RNA solution is poured into the affinity chromatography column which contains the specific oligo (dt) cellulose (as seen in FIG. 1). The column is then washed twice in modulated volume of wash buffer, thus, the tRNA, rRNA and other residual will be eluted. Finally, eluting the mRNA from the column with modulate elution buffer, then the pure mRNA is isolated. But there are disadvantages in the aforesaid protocols of mRNA purification.

(1) The range of application is narrow. That is, the traditional design is suitable to the eukaryotic cells, but not suit for the prokaryotic cells. Because the mRNA of prokaryotic cells without the pol (A) tail structure, mRNA can not to be separated between tRNA and rRNA by the hydrogen-bond binding of Adenine and Thymidine in the affinity column.

(2) The protocols are complicated, costly and time consuming to operate. Beside, it is easy to suffer the contamination of RNase during the operation.

(3) The RNA separation apparatus takes up a lot of laboratory space. Furthermore, the isolated mRNA sample can not be tested continuously in the biochemical analysis and automation process.

As the above description, the traditional protocols of mRNA purification still exist some space of improvements.

SUMMARY OF THE INVENTION

The first objective of the present invention is to provide a device and method for the specific mRNA purification of prokaryotic cells by utilizing the microfluidic chip which comprises tRNA and rRNA probes of reaction region, transition region, waste region, pneumatic actuator and a heater device. It can discard tRNA and rRNA and purify a high concentration of mRNA by repeated hybridization reaction in the reaction region.

The second objective of the present invention is to provide a simple and easy operation, and to avoid the contamination of RNase.

The third objective of the present invention is to establish a microdevice, which is portable and can be operated rapidly and repeatedly by utilizing a microfluidic chip.

For your esteemed members of reviewing committee to further understand and recognize the objectives, the characteristics, and the functions of the invention, a detailed description in matching with corresponding drawings are presented as the following.

BRIEF DESCRIPTION OF THE DRAWINGS

The objects, spirits and advantages of the preferred embodiments of the present invention will be readily understood by the accompanying drawings and detailed descriptions, wherein.

DETAILED DESCRIPTION OF THE PRESENT INVENTION

Figure 1:
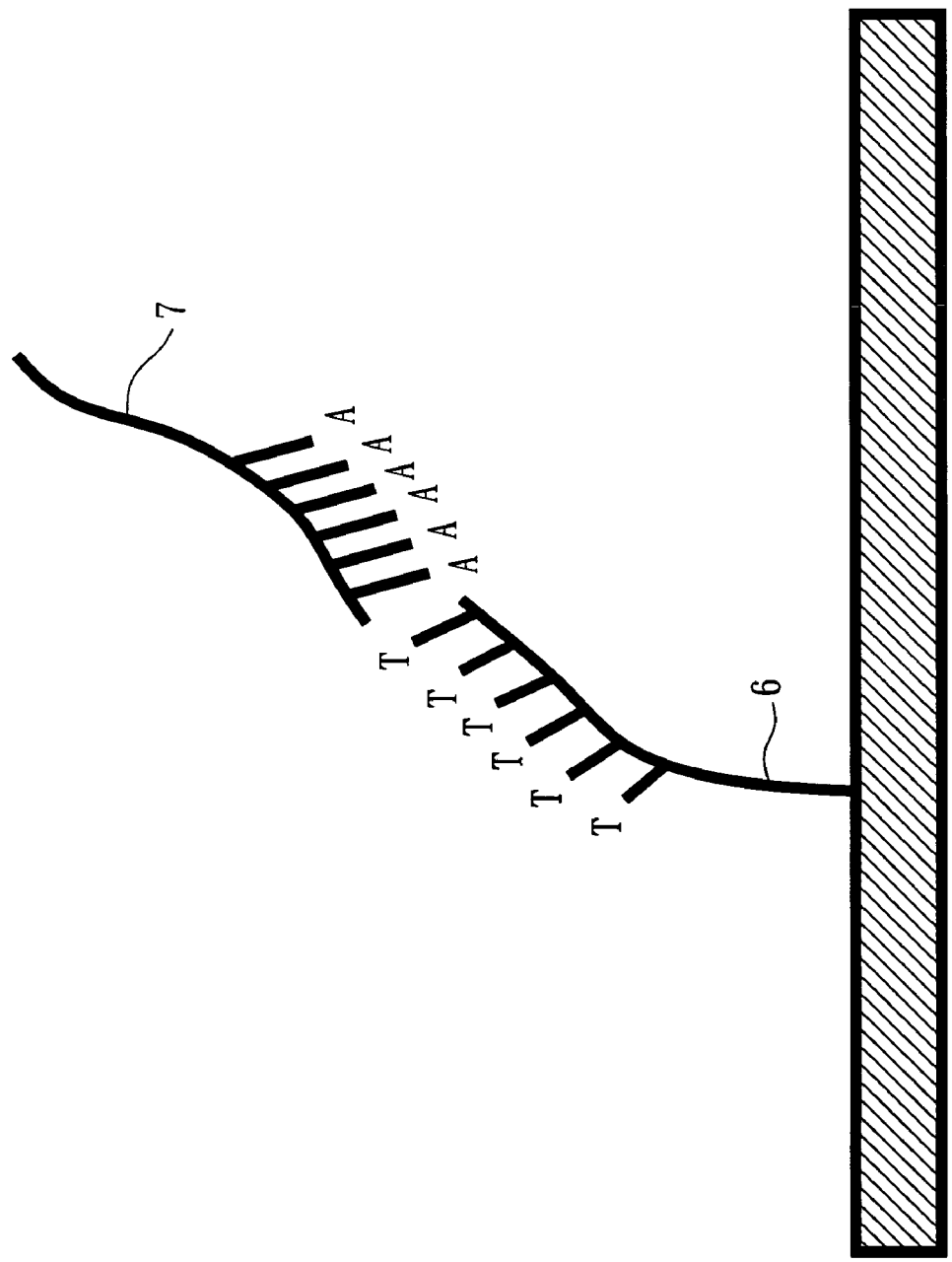
FIG. 1 is a schematic diagram showing the mRNA hybridization of eukaryotic cells.
Figure 2:
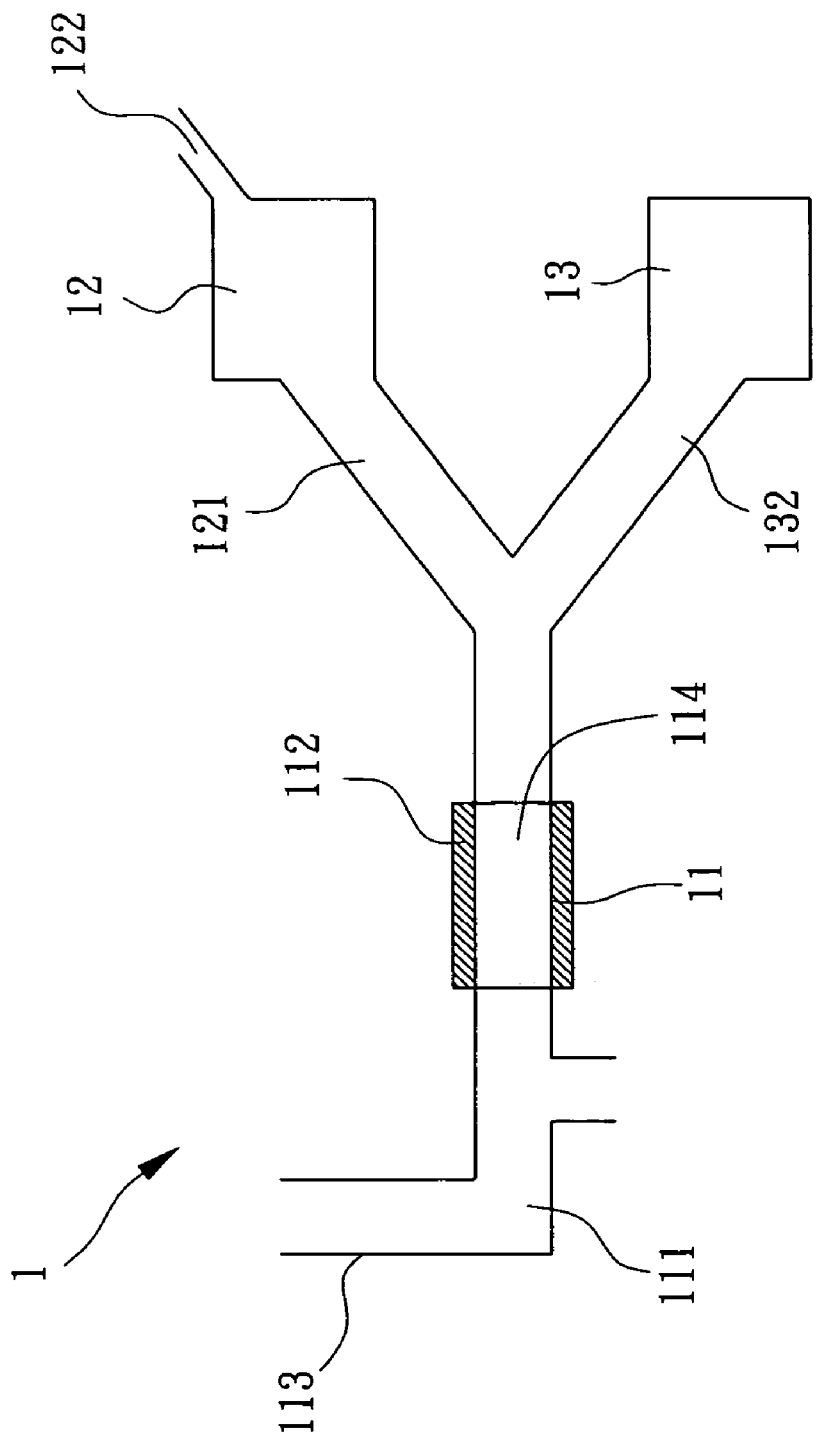
FIG. 2 is a schematic diagram showing the briefly structure of RNA separation device of the present invention.
Figure 3:
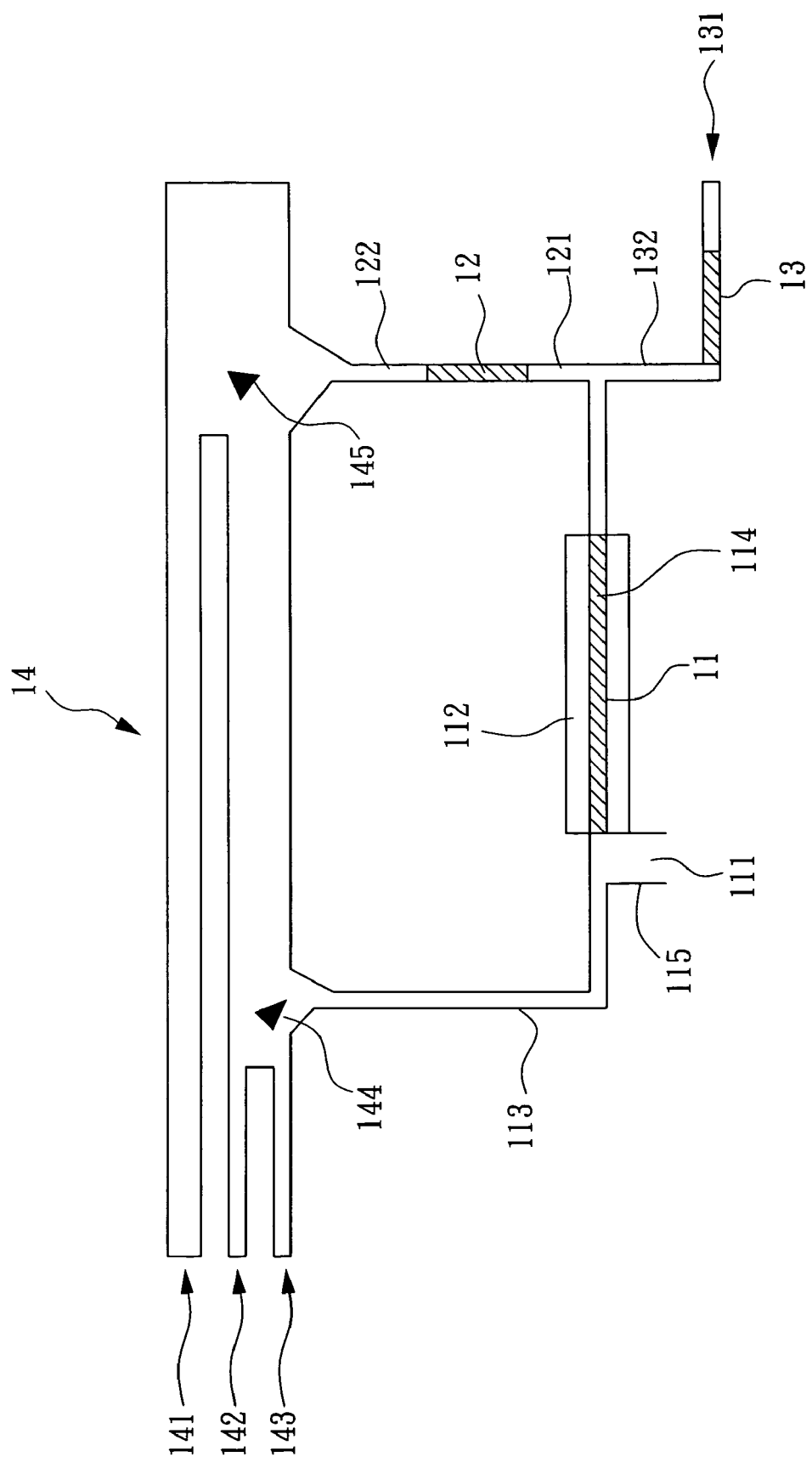
FIG. 3 is a top view of a preferred embodiment of the present invention.

The present invention is described in more detail in the following elucidations. These methods, operations and functions are given by way of illustration and are not intended to limit the invention in any way. Please refer to FIGS. 2, 3 and 4. As shown, a microfluidic chip of a preferred embodiment of the present invention comprises specific tRNA and rRNA probes of reaction region (11), transition region (12), waste region (13) and pneumatic actuator (14). Wherein, the reaction region (11) comprises an inlet (111) as an entrance way of reaction solution (2) and buffer solution (3), and the covalent linking of rRNA or/and tRNA as a probe. The reaction solution (2) contains the total RNAs of prokaryotic cells. The reaction region (11) further comprises a heater device (112) which is chosen from the hot plate, heater, microwave and infrared rays, that can modulate the temperature to a moderate condition for hybridization or denature. The transition region (12) is connected to the reaction region (11) by the airflow channel 1 (121) for stocking the remainder of reaction solution (2). The waste region (13) is connected to the reaction region (11) by the airflow channel 2 (132) and, in one side of the waste region (13), there is a waste outlet (131) for discarding the buffer solution (3) after reacting in the reaction region (11).

The pneumatic actuator (14) comprises an airflow channel 1 (141), an airflow channel 2 (142), an airflow channel 3 (143), a disturbed triangular block 1 (144) and a disturbed triangular block 2 (145). The pneumatic actuator (14) is also connected with the liquid inlet (111) of reaction region (11) by the airflow channel 3 (113), and connected with the transition region (12) by the airflow channel 4 (122). Navier-Stokes (pressure and velocity) equation is directly applied in the pneumatic actuator operation. Utilizing the different flow rate of airflow channel and the disturbed triangular blocks to generate the different pressure disturbance in the airflow channel. After then, the pneumatic device will generate the suction, exclusion and static effect and can control the microfluid to divide, combine and turn among the reaction region (11), the transition region (12) and the waste region (13).

When the total prokaryotic RNA solution (2) and the buffer solution (3) are injected into the liquid inlet (111) of the reaction region (11), the airflow (5) will be introduced to the airflow channel 2 (142) and the airflow channel 3 (143). Because of effect of two disturbed blocks, the airflow (5) flows to the disturbed triangular block 19 (144) and the disturbed triangular block 2 (145) will introduce a exclusion (flow up to down direction) in the airflow channel 3 (113) and channel 4 and cause the reaction solution (2) and buffer solution (3) move block, front or stop in the reaction region (11) by adjusting the airflow rates.

As seen in FIG. 4, the heater device (112) is used for increasing the temperature of the reaction region to 40° C. for hybridization, so that the rRNA or tRNA of the reaction solution (2) is promoted to hybridize with the probes of reaction region (11). The airflow (5) will be introduced to the airflow channel 1 (141), channel 2 (142) and channel 3 (143). Because of the effect of two disturbed blocks, the airflow (5) flows to the disturbed triangular block 1 (144) and the disturbed triangular block (145) will introduce an exclusion in airflow channel 3 (113) and a suction (from down to up direction) in airflow channel 4 (122) and cause the remainder of reaction solution (2) to be transferred to the transition region (12) (FIG. 4C). Following, the new buffer solution (3) is injected into the reaction, and the heated device (112) is started for increasing the temperature of the reaction region (11) to 70° C.~100° C. for denaturing, and promoting the prokaryotic rRNA or tRNA to departure from the probes of the reaction region (11). Modulating the ratio of airflow (5) in the airflow channel 2 (142) and channel 3 (143) and control the above buffer solution (3) move to the waste region (13) become a waste solution. Finally, the waste solution was discarded using the waste outlet (131) (as seen in FIG. 4E).

Figure 4A:
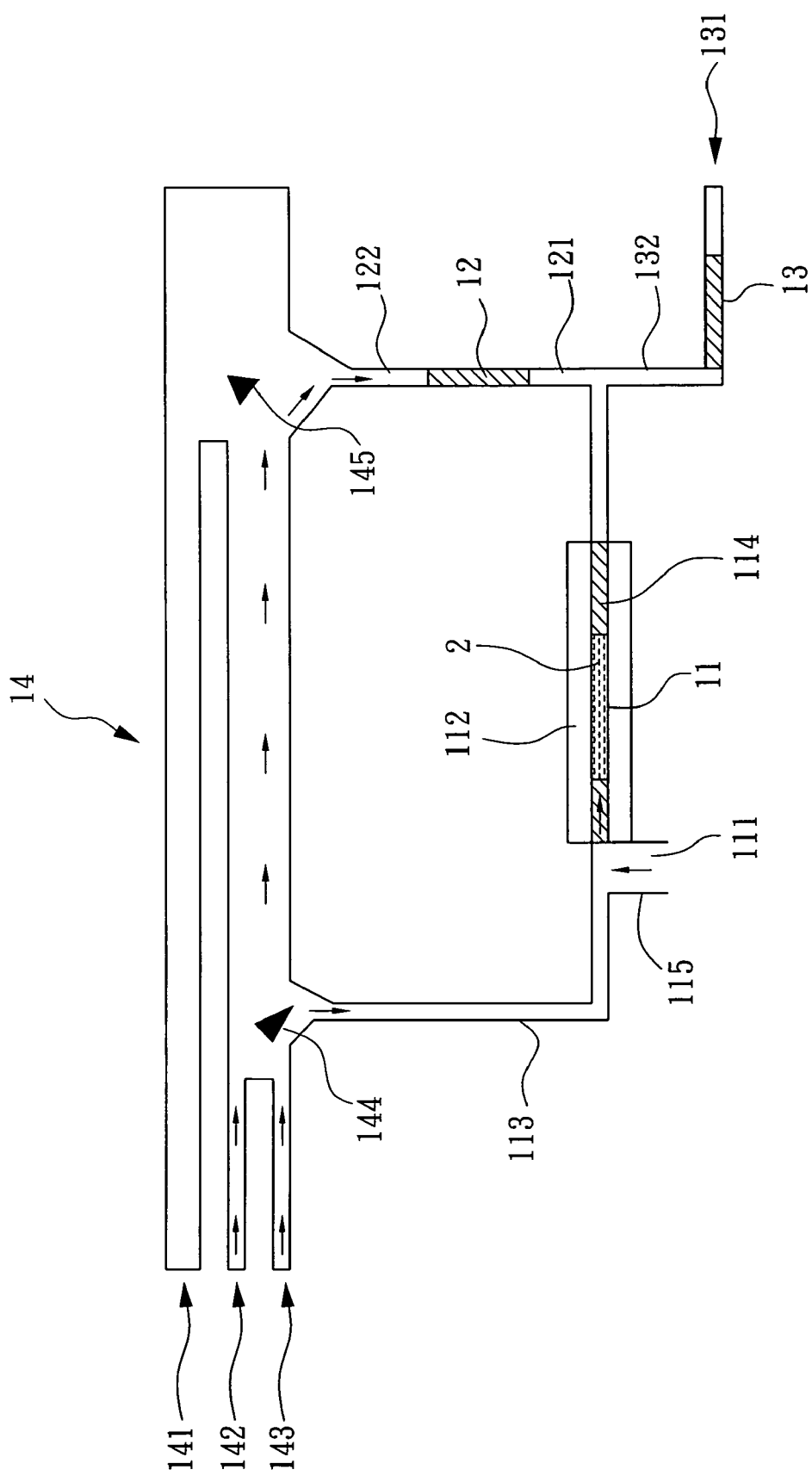
FIGS. 4A, B and C are flowcharts respectively showing the procedures of the injection of reaction solution and buffer solution, rapid hybridization reaction and transfer the remainder of reaction solution to the transition region.
Figure 4B:
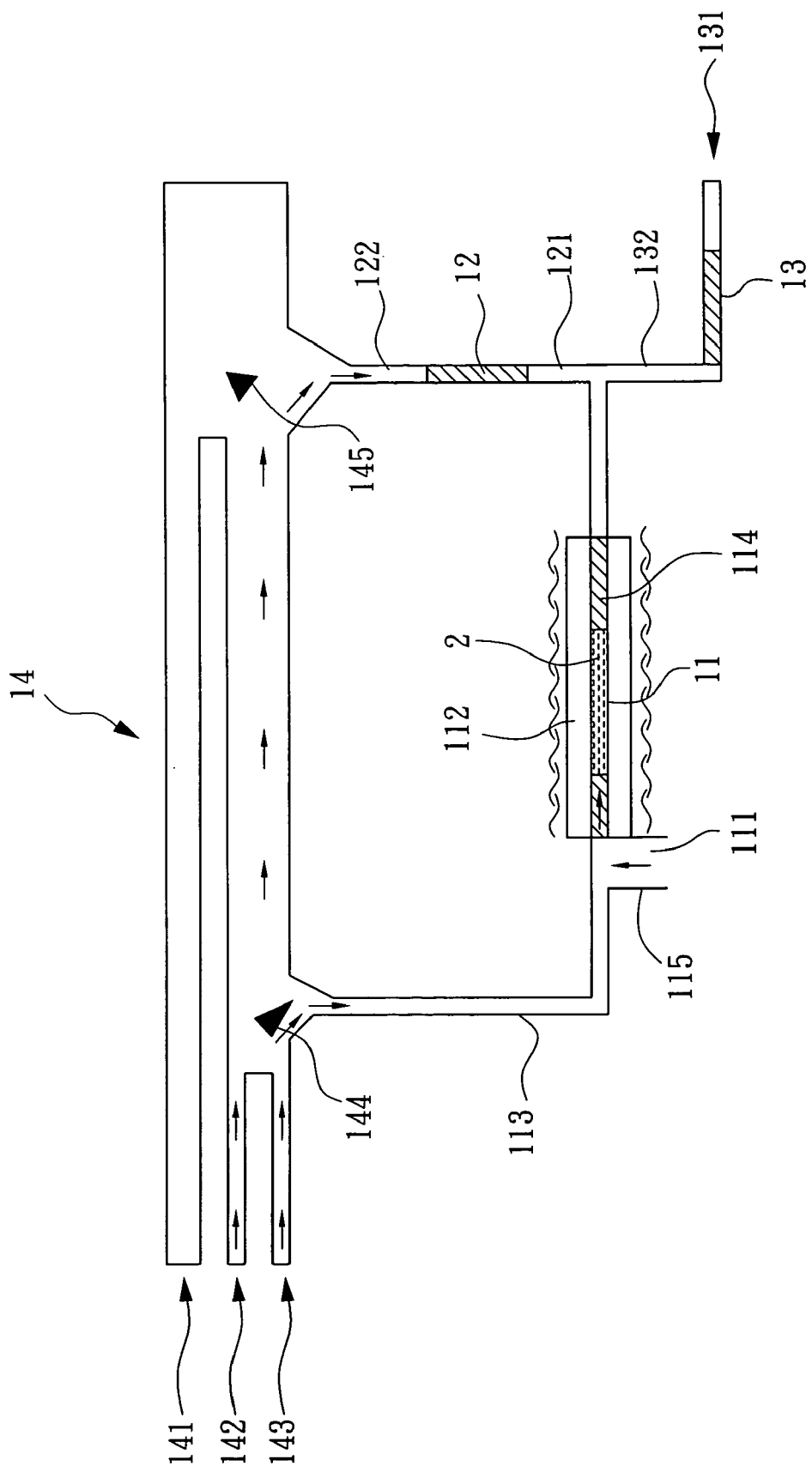
FIGS. 4D, E and F are flowcharts respectively showing the procedures of the denature heating of reaction region, transfer the waste solution of reaction region to the waste region and transfer the remainder of reaction solution from the transition region to reaction region.
Figure 4C:
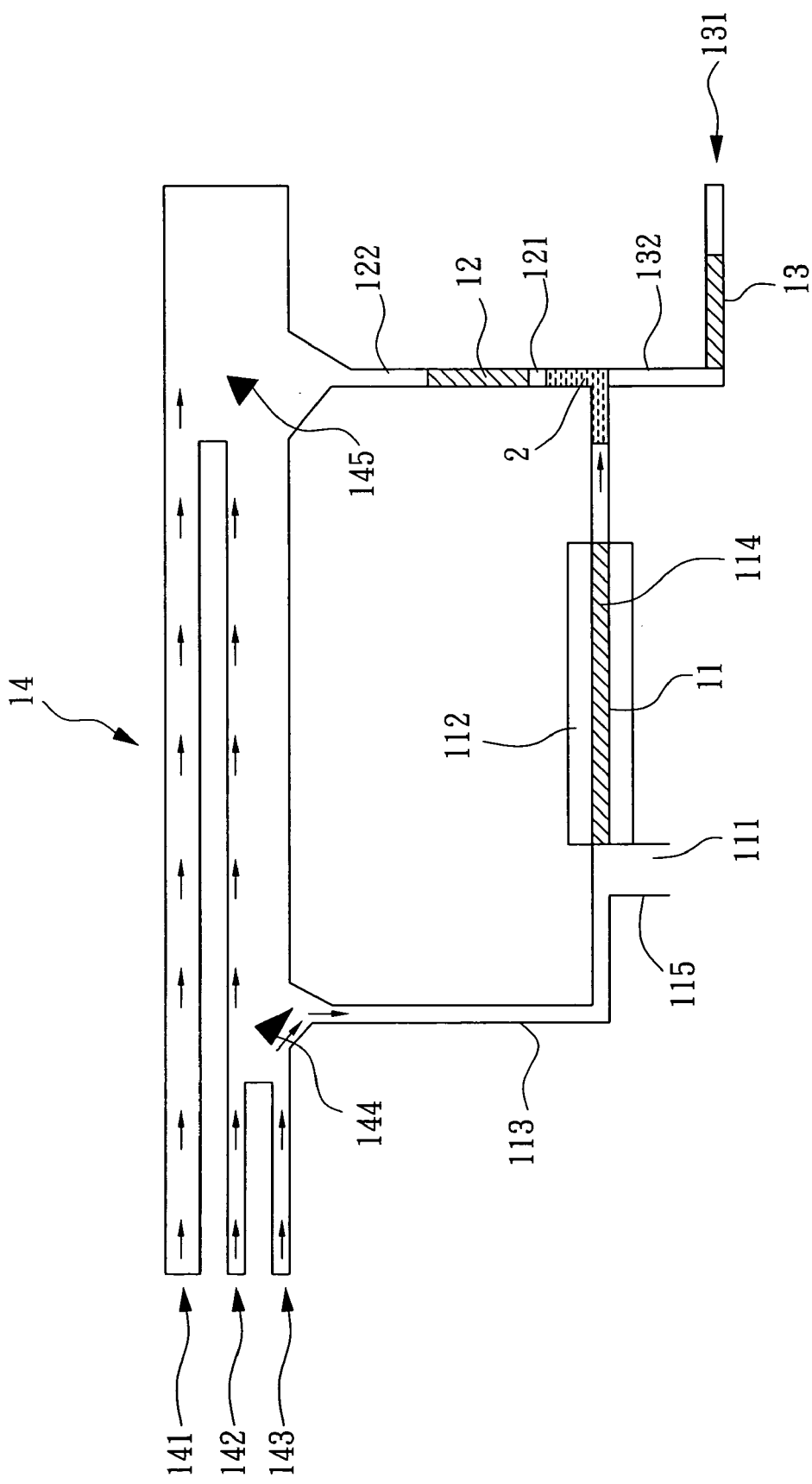
Figure 4D:
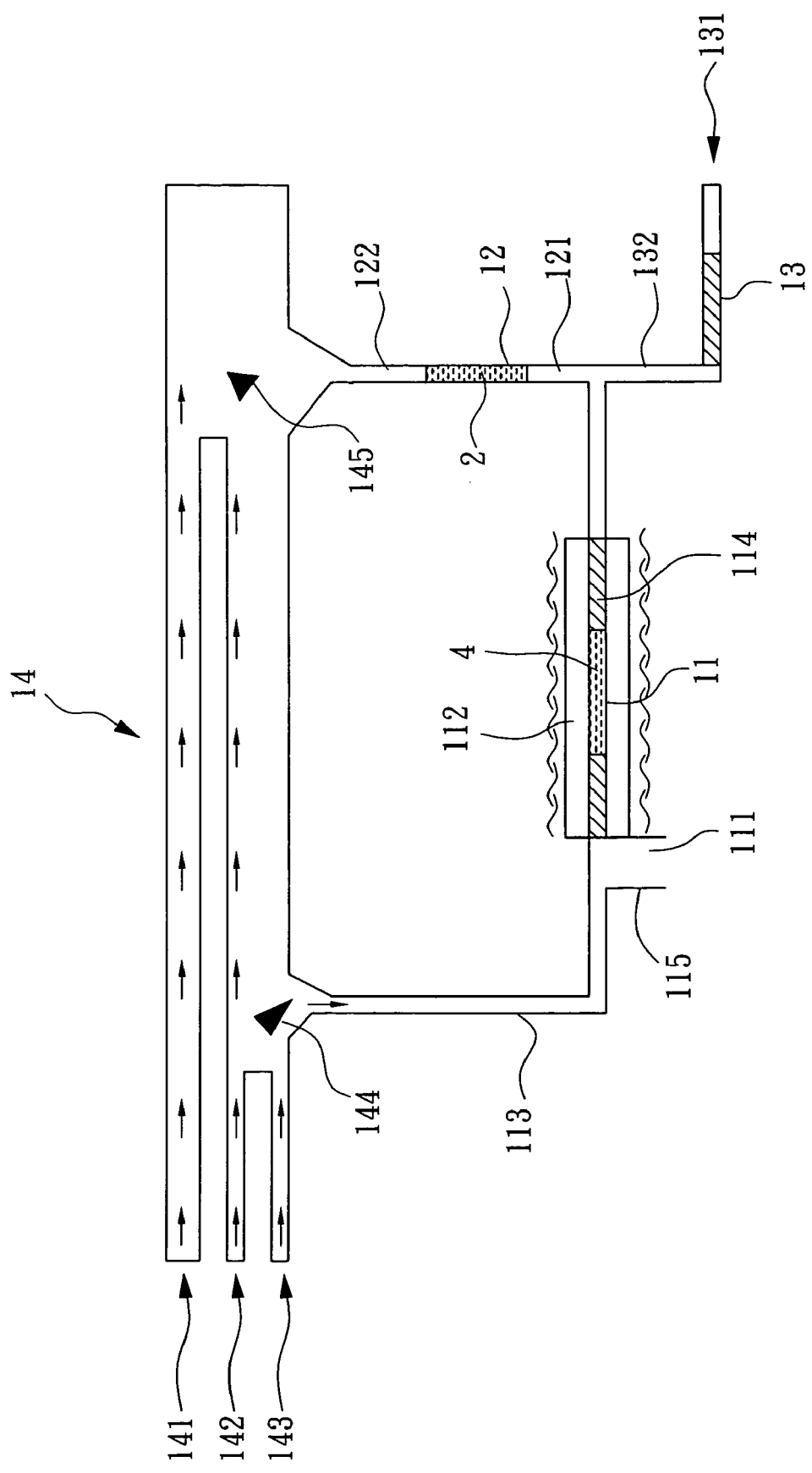
Figure 4E:
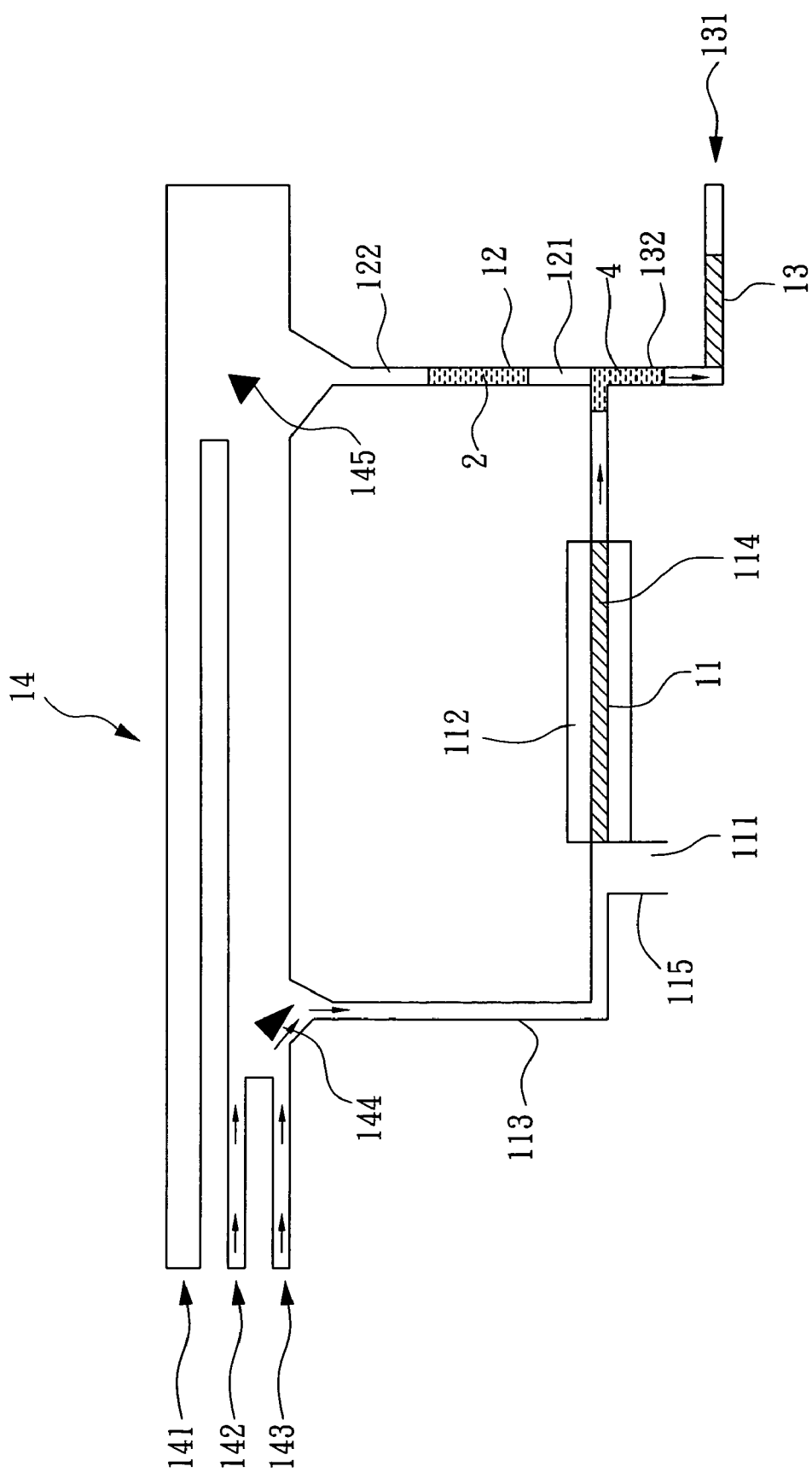
Figure 4F:
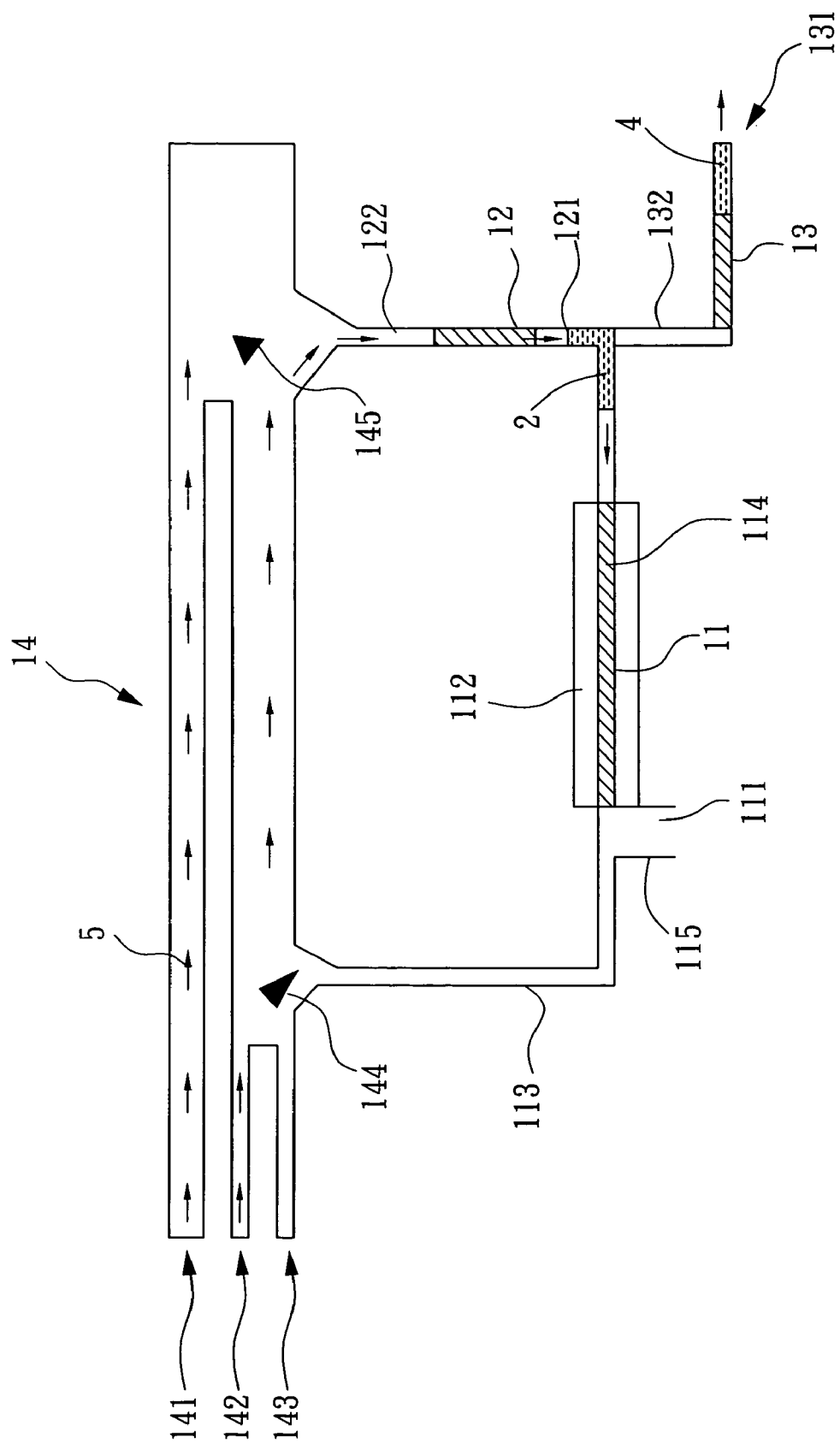

The ration of airflow (5) is changed and modulated in the airflow channel 1 (141) and channel 2 (142). Because of the effect of two disturbed blocks, it will introduce a suction in the liquid channel (113) and an exclusion in the liquid channel (122), and then promote the remainder solution of transition region (12) to flow back into the reaction region (11) (as seen in FIG. 4F). The same process of by hybridization is continued to repeat many times until most of rRNA and tRNA are eluded in the reaction region (11). The experimental results showed that one can get 3.8 times more then the traditional method at the same time by utilizing the repeat operation of RNA separation device.

One can understand from above that the present invention has the advantage of effective discarding the non-specific bonding and getting a high purity of prokaryotic mRNA. Besides, the device and method of the present invention is easy and fast for repetitious operation, effective avoiding RNase contamination, is simple and easy to set up in terms of equipment, takes up virtually no floor space, is suited to microdevices for biochemical analysis which is easy to connect to outside the chip system for the next step of analysis. Thus, the present invention is a practice solution to the RNA separation problem and a valuable invention for commercial use. The foregoing description should be taken as illustrative and not limiting in any sense. Other embodiment of the invention will occur to those skilled in the art and are within the scope of the following claims.

While the present invention has been shown and described with reference to a preferred embodiment thereof, and in terms of the illustrative drawings, it should be not considered as limited thereby. Various possible modification, omission, and alterations could be conceived of by one skilled in the art to the form and the content of any particular embodiment, without departing from the scope and the sprit of the present invention.

What is claimed is:

1. An mRNA separation method, comprising the steps of:
   (a) injecting a reaction solution into a reaction region which contains a covalent linking of a tRNA probe and a covalent linking of an rRNA probe for hybridizing tRNA and rRNA in the reaction solution;
   (b) adjusting a moderate hybridization temperature in the reaction region to hybridize the tRNA and the rRNA in the reaction solution;
   (c) moving the reaction solution in the reaction region after hybridization to a transition region by a pneumatic actuator;
   (d) adding a buffer solution to the reaction region, and heating the reaction region to a moderate denature temperature such that the tRNA and the rRNA hybridized by the tRNA probe and the rRNA probe depart from the tRNA probe and rRNA probe into the buffer solution;
   (e) moving the buffer solution with the departed tRNA and rRNA in the reaction region after denature step (d) to a waste region by the pneumatic actuator to discard the departed tRNA and rRNA;
   (f) moving the reaction solution in the transition region in the step (c) back to the reaction region by the pneumatic actuator; repeatedly performing the steps (a) through (f) so as to purify mRNA in the reaction solution;
   wherein the steps (a) through (f) are performed on a microfluidic chip.

2. The mRNA separation method of claim 1, wherein the step (d) of heating the reaction region to the moderate denature temperature includes heating the reaction region to the moderate denature temperature by a heating apparatus, the heating apparatus being selected from the group consisting of a hot plate, a heater, microwave and infrared rays.

3. The mRNA separation method of claim 1, wherein the moderate hybridization temperature is 40° C.

4. The mRNA separation method of claim 1, wherein the moderate denature temperature is between 7020 C and 100° C.

5. The mRNA separation method of claim 1, wherein the mRNA separation method is carried out by using a pneumatic device which can generate the suction, exclusion and static effect to control the microfluid for dividing, combining and turning among the region region, the transition region and the waste region.

6. The mRNA separation method of claim 1, wherein the step (a) of injecting the reaction solution into the reaction region includes injecting the reaction solution into the reaction region of the micro fluidic chip.

7. The mRNA separation method of claim 1, wherein the step (c) of moving the reaction solution to the transition region includes moving the reaction solution to the transition region of the microfluidic chip.

8. The mRNA separation method of claim 1, wherein the step (e) of moving the buffer solution to the waste region includes moving the buffer solution to the waste region of the microfluidic chip.

* * * * *